United States Patent [19]

Howe

[11] 4,129,568

[45] Dec. 12, 1978

[54] 2-[3-ARYL-2-ISOXAZOLIN-5-YL]BENZO-ATES

[75] Inventor: Robert K. Howe, Bridgeton, Mo.

[73] Assignee: Monsanto Company, St. Louis, Mo.

[21] Appl. No.: 828,445

[22] Filed: Aug. 29, 1977

Related U.S. Application Data

[63] Continuation-in-part of Ser. No. 796,110, May 12, 1977, abandoned.

[51] Int. Cl.$^2$ .......................................... C07D 263/14
[52] U.S. Cl. .................................. 260/307 F; 71/76; 71/88; 260/307 H; 260/566 D
[58] Field of Search ....................................... 260/307 F

[56] References Cited

U.S. PATENT DOCUMENTS 4,032,644  6/1977  Nadelson .............................. 424/272

*Primary Examiner*—Raymond V. Rush
*Attorney, Agent, or Firm*—Richard H. Shear; Donald W. Peterson

[57] ABSTRACT

2-[3-aryl-2-isoxazolin-5-yl]benzoates and their use as intermediates for agricultural chemicals. The subject isoxazolines can be converted to the corresponding isoxazoles. The latter are useful as herbicides and as plant growth regulants.

4 Claims, No Drawings

2-[3-ARYL-2-ISOXAZOLIN-5-YL]BENZOATES

This is a continuation-in-part of copending application Ser. No. 796,110, filed May 12, 1977, now abandoned.

The invention relates to novel 2-[3-aryl-2-isoxazolin-5-yl]benzoates and their use in the preparation of 2-[3-aryl-5-isoxazolyl]benzoates having the formula

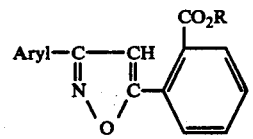

wherein R is defined below. The latter compounds are effective agricultural chemicals such as herbicides and plant growth regulants as disclosed in my copending application Ser. No. 796,248, filed May 12, 1977.

Said application discloses that when the 2-[3-aryl-5-isoxazolyl]-benzoates are used as a herbicide, it is desirable that rates of application above 2.24 kilograms per hectare be utilized. When used to regulate the growth of desirable plants, rates below 5.6 kilograms per hectare especially 0.056 to 3.36 are preferred.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth, it does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

The 2-[3-aryl-2-isoxazolin-5-yl]benzoates of the invention may be represented by the formula

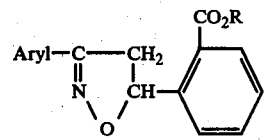

wherein R is selected from the group consisting of hydrogen, lower alkyl and agriculturally acceptable cations.

The term "agriculturally acceptable cations" is understood to mean those cations which are commonly used in agricultural compositions to form the salt of the free acid, including but not limited to the alkali metal, substituted amine and ammonium cations.

In accordance with the novel aspects of the present invention, the (isoxazolin-5-yl)benzoates may be prepared in accordance with the following reaction scheme:

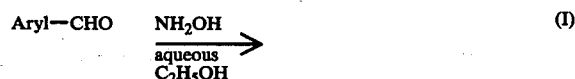

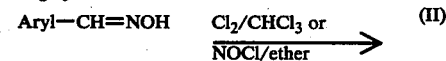

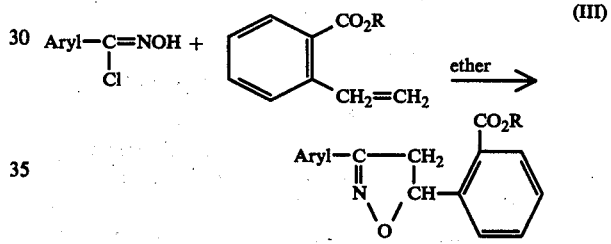

As is apparent to those skilled in the art, the appropriate hydroxamoyl chloride (III) is prepared by reacting hydroxylamine with an aryl aldehyde in aqueous alcohol to form Compound II which is then chlorinated to the hydroxamoyl chloride (III). Addition of o-vinylbenzoate to the hydroxamoyl chloride under basic conditions (such as in the presence of tertiary amines) will result in the (isoxazolin-5-yl)benzoates of the invention.

Aryl aldehydes may be prepared by the procedure of Jolad and Rajagopal, *Org. Syn. Coll.*, Vol. V, Page 139 (1973). The o-vinylbenzoate may be prepared by treatment of vinylbenzoic acid with thionyl chloride and then with methanol. o-Vinyl-benzoic acid may be prepared in accordance with the following examples which are presented as an illustration of the above procedure.

EXAMPLE 1

Preparation of o-Vinylbenzoic Acid

The sodium salt of 2-carboxybenzaldehyde was prepared by addition of 129.6 g (0.60 mol) of 25% sodium methoxide in methanol to a solution of 90 g (0.6 mol) of 2-carboxybenzaldehyde in 900 ml of methanol, followed by concentration under vacuum to 90° C. at 0.5 torr.

Methylenetriphenylphosphorane was prepared on a 0.605 mol scale in dimethylsulfoxide from methyltriphenylphosphonium bromide and dimsylsodium as described in E. J. Corey et al, *J. Org. Chem.*, Vol. 28, Page 1128 (1963). Then the sodium carboxylate was added with stirring under N$_2$. After a few minutes, the solution was concentrated under oil pump vacuum (45° C. maximum bath temperature), and water was added to the residue. The mixture was filtered, and to the filtrate was added 57 ml of concentrated HCl with stirring. The resultant mixture was extracted with ether. The ether solution was extracted with 5% NaOH. The aqueous layer was acidified with HCl and then extracted with ether. The ether solution was dried and concentrated under vacuum to 61 g (69%) of sticky solid. A small portion was recrystallized from pet ether to give 1.5 g of solid, mp 89°-90° C.

EXAMPLE 2

Preparation of Methyl o-Vinylbenzoate

A mixture of 58.5 g (.395 mol) of o-vinylbenzoic acid and 127.3 g (1.08 mol) of thionyl chloride was heated on a steam bath (strong gas evolution) for 40 minutes until gas evolution subsided. The solution was concentrated, and 270 ml of methanol was added slowly. The mixture was held at reflux for 10 minutes and then was concentrated. Ether was added to the residue, and the solution was extracted three times with water. The ether layer was dried, a little hydroquinone was added, and the solution was distilled to give 32.2 g (50.5%) of liquid.

EXAMPLE 3

Preparation of Methyl 2-[3-[3-(Trifluoromethyl)Phenyl]-2-Isoxazolin-5-yl]Benzoate A solution of 8.67 g (0.0858 mol) of triethylamine in 25 ml of ether was added dropwise with stirring to a solution of 19.19 g (0.0858 mol) of m-trifluoro-methylbenzohydroxamoyl chloride and 13.9 g (0.0858 mol) of methyl o-vinylbenzoate in 200 ml of ether at 0°-5° C. during 45 minutes. The mixture was stirred in an ice bath for 2 hours and then at 20° C. for 21 hours, and then was washed three times with water. The ether layer was filtered to remove a little gelatinous solid, and the filtrate was dried (CaSO$_4$) and concentrated under vacuum to 10 torr at 60° C. to give 29.5 g (98%) of oil. The nmr spectrum showed this to be fairly pure product; nmr (CDCl$_3$) δ 8.18-7.23 (m, 8, ArH), 6.53 (dd, 1, 5-H), 4.10 (dd, 1, 4-H), 3.93 (s, 1, CH$_3$), 3.13 (dd, 1, 4-H).

EXAMPLE 4

Preparation of Methyl 2-[3-Phenyl-2-Isoxazolin-5-yl]-Benzoate

To a stirred solution of 9.4 g (0.0604 mol) of benzaldehyde chlorooxime and 10.76 g (0.0664 mol) of methyl o-vinyl-benzoate in 100 ml of ether at 0°-5° C. was added dropwise a solution of 7.81 g (0.0604 mol) of ethyldiisopropylamine in 35 ml of ether during 30 minutes. The mixture was stirred in an ice bath for 4 hours, diluted with another 400 ml of ether, extracted three times with water, and concentrated under vacuum to a solid. This solid was washed with 200 ml of hexane. The undissolved solid product, 14.21 g, had mp 90°-94° C. Crystallization of this from 100 ml of methanol gave 13.50 g (79%) of white solid, mp 93.5°-95° C.

Anal. Calc'd. for C$_{17}$H$_{15}$NO$_3$: C, 72.58; H, 5.37. Found: C, 72.50; H, 5.38.

EXAMPLE 5

Preparation of Methyl 2-[3-(1-Naphthyl)-2-Isoxazolin-5-yl]Benzoate

To a solution of 15.0 g (0.0926 mol) of methyl o-vinylbenzoate and 19.04 g (0.0926 mol) of 1-naphthaldehyde chlorooxime in 250 ml of ether was added dropwise a solution of 9.35 g (0.0926 mol) of triethylamine in 50 ml of ether during 30 minutes with stirring at 0°-5° C. The mixture was stirred at 0°-5° C. for another 1.5 hours and then was allowed to stand overnight. Ether, 150 ml, was added and the mixture was extracted three times with water. The ether layer was dried (CaSO$_4$) and concentrated under vacuum to 130° C. at 0.2 torr on a Kugelrohr apparatus to give 19.3 g of residue. This material was boiled with 200 ml of methanol. The methanol was decanted from insoluble material and cooled to give 4.55 g of solid product. Recrystallization of the product gave 3.63 g of solid, mp 110.5-112.5° C.

Anal. Calc'd. for C$_{21}$H$_{17}$NO$_3$: C, 76.12; H, 5.17. Found: C, 76.05; H, 5.18.

Another 4.44 g of pure product, mp 111°-112.5° C., was obtained by chromatography of the methanol-insoluble material on silica gel with benzene and crystallization of the resultant product from methanol.

Acids may be prepared by hydrolysis of the appropriate ester, e.g., refluxing HCl-acetic acid.

Salts may be prepared by adding the acid to the appropriate base in water.

As used herein, the term "lower alkyl" or "lower alkoxy" is understood to mean those alkyl or alkoxy groups having from 1 to 5 carbon atoms, inclusive.

As used herein, the term "Aryl" is meant to include naphthyl, phenyl, phenyl substituted by one or more halogen, trifluoromethyl, lower alkyl or lower alkoxy moieties.

Preferred are those compounds in which Aryl is phenyl or phenyl substituted by one or two halogen, trifluoromethyl, lower alkyl or lower alkoxy moieties. Further preferred are those in which R is lower alkyl.

The novel (isoxazolin-5-yl) benzoates of the invention may be converted to the isoxazolyl benzoates by reaction with N-bromosuccinimide or dichlorodicyanobenzoquinone. More specifically, the isoxazol-5-yl-benzoates disclosed in Ser. No. 796,248 may be prepared by reacting the appropriate hydroxamoyl chloride with an o-vinylbenzoate under basic conditions (such as in the presence of tertiary amines) to form the isoxazolin-5-yl-benzoate which can then be converted to the isoxazol-5-yl-benzoate either upon heating with N-bromosuccinimide or dichlorodicyanobenzoquinone. In order to clarify the above, the following reaction scheme is presented:

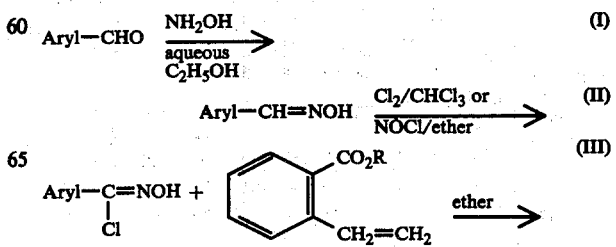

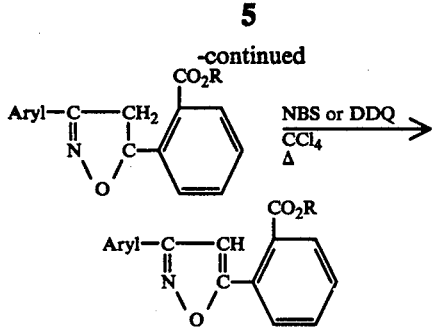

As is apparent to those skilled in the art, the appropriate hydroxamoyl chloride is prepared in accordance with the above reaction scheme by reaction of hydroxylamine with an aryl aldehyde in aqueous alcohol to form Compound II which can then be chlorinated to the hydroxamoyl chloride (III).

Aryl aldehydes may be prepared by the procedure of Jolad and Rajagopal, Org. Syn. Coll., Vol. V, Page 139 (1973). The o-vinylbenzoate may be prepared by treatment of vinylbenzoic acid with thionyl chloride and then with an alcohol. Examples of this procedure are set out in Ser. No. 796,248, which is hereby incorporated by reference.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula wherein Aryl is selected from the group consisting of naphthyl, phenyl, phenyl substituted by one or more halogen, trifluoromethyl, lower alkyl or lower alkoxy moieties and R is selected from the group consisting of hydrogen, lower alkyl and agriculturally acceptable cations.

2. A compound according to claim 1 wherein Aryl is phenyl or phenyl substituted by one or two halogen, trifluoromethyl, lower alkyl or lower alkoxy moieties.

3. A compound according to claim 1 wherein R is lower alkyl.

4. A compound according claim 1 wherein Aryl is naphthyl.